(12) United States Patent
Paul et al.

(10) Patent No.: US 11,763,450 B1
(45) Date of Patent: Sep. 19, 2023

(54) MITIGATING ADVERSARIAL ATTACKS ON MEDICAL IMAGING UNDERSTANDING SYSTEMS

(71) Applicants: University of South Florida, Tampa, FL (US); H. LEE MOFFITT CANCER CENTER AND RESEARCH INSTITUTE, INC., Tampa, FL (US)

(72) Inventors: Rahul Paul, Tampa, FL (US); Dmitry Goldgof, Lutz, FL (US); Lawrence Hall, Tampa, FL (US); Matthew Schabath, Tampa, FL (US); Robert Gillies, Tampa, FL (US)

(73) Assignees: UNIVERSITY OF SOUTH FLORIDA, Tampa, FL (US); H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 119 days.

(21) Appl. No.: 17/099,372

(22) Filed: Nov. 16, 2020

Related U.S. Application Data

(60) Provisional application No. 62/991,715, filed on Mar. 19, 2020, provisional application No. 62/935,179, filed on Nov. 14, 2019.

(51) Int. Cl.
*G06T 7/00* (2017.01)
*G06F 16/55* (2019.01)
(Continued)

(52) U.S. Cl.
CPC ............ *G06T 7/0012* (2013.01); *G06F 16/55* (2019.01); *G06F 18/214* (2023.01);
(Continued)

(58) Field of Classification Search
CPC ....... G06T 7/0012; G16H 30/20; G06F 16/55; G06F 21/566
See application file for complete search history.

(56) References Cited

U.S. PATENT DOCUMENTS 10,757,292 B1 * 8/2020 Sung .................... G06T 1/0021
11,138,724 B2 * 10/2021 Nakano ................ G06K 9/6274
(Continued)

OTHER PUBLICATIONS

Finlayson et al., "Adversarial Attacks Against Medical Deep Learning Systems," Feb. 4, 2019, 9 pages, Cornell University.
(Continued)

*Primary Examiner* — Edward Park
(74) *Attorney, Agent, or Firm* — QUARLES & BRADY LLP

(57) ABSTRACT

The present disclosure describes a multi-initialization ensemble-based defense strategy against an adversarial attack. In one embodiment, an exemplary method includes training a plurality of conventional neural networks (CNNs) with a training set of images, wherein the images include original images and images modified by an adversarial attack; after training of the plurality of conventional neural networks, providing an input image to the plurality of conventional neural networks, wherein the input image has been modified by an adversarial attack; receiving a probability output for the input image from each of the plurality of conventional neural networks; producing an ensemble probability output for the input image by combining the probability outputs from each of the plurality of conventional neural networks; and labeling the input image as belonging to one of the one or more categories based on the ensemble probability output.

20 Claims, 21 Drawing Sheets

Table 1: CNN architectures and parameters

| CNN architecture 1 | | CNN architecture 2 | | CNN architecture 3 | |
|---|---|---|---|---|---|
| Layers | Parameters | Layers | Parameters | Layers | Parameters |
| Input | 100 x 100 | Input | 100 x 100 | Left BRANCH | |
| Conv1 | 64x5x5,pad 0,stride 1 | Conv1 | 64x5x5,pad 0,stride 1 | Input | 100 x 100 |
| Leaky ReLU | alpha=0.01 | Leaky ReLU | alpha=0.01 | Max Pool 1 | 10x10 |
| Max Pool 1 | 3x3, stride 3, pad 0 | Max Pool 1 | 3x3, stride 3, pad 0 | Dropout | 0.1 |
| Conv2 | 64x2x2,pad 0,stride 1 | Conv2 | 64x2x2,pad 0,stride 1 | Left BRANCH | |
| Leaky ReLU | alpha=0.01 | Leaky ReLU | alpha=0.01 | Conv1 | 64x5x5,pad 0,stride 1 |
| Max Pool 2 | 3x3, stride 3, pad 0 | Max Pool 2 | 3x3, stride 3, pad 0 | Leaky ReLU | alpha=0.01 |
| Dropout | 0.1 | Dropout | 0.1 | Max Pool 2 | 3x3, stride 3, pad 0 |
| FC 1+ ReLU | 128 | FC 1+ ReLU | 128 | Conv2 | 64x2x2,pad 0,stride 1 |
| FC 2+ ReLU | 8 | LSTM 1 + ReLU | 8 | Leaky ReLU | alpha=0.01 |
| L2 regularizer | 0.01 | L2 regularizer | 0.01 | Max Pool 3 | 3x3, stride 3, pad 0 |
| Dropout | 0.25 | Dropout | 0.25 | Merge Left and Right | |
| FC 3+ Sigmoid | 1 | FC 3 + Sigmoid | 1 | Conv 3 | 64x2x2, pad 0, stride 1 |
| | | | | Max Pool 4 | 2x2, stride 2, pad 0 |
| | | | | L2 regularizer | 0.01 |
| | | | | Dropout | 0.1 |
| | | | | FC 1+ Sigmoid | 1 |
| Total parameters | 841,681 | Total parameters | 845,033 | Total parameters | 39,553 |

(51) Int. Cl.
*G16H 30/20* (2018.01)
*G06N 3/08* (2023.01)
*G06F 18/214* (2023.01)
*G06F 18/25* (2023.01)
*G06F 18/2415* (2023.01)
*G06N 3/045* (2023.01)

(52) U.S. Cl.
CPC ........ *G06F 18/2415* (2023.01); *G06F 18/254* (2023.01); *G06N 3/045* (2023.01); *G06N 3/08* (2013.01); *G16H 30/20* (2018.01); *G06T 2200/04* (2013.01); *G06T 2207/10081* (2013.01); *G06T 2207/20076* (2013.01); *G06T 2207/20081* (2013.01); *G06T 2207/20084* (2013.01)

(56) References Cited

U.S. PATENT DOCUMENTS

| | | | |
|---|---|---|---|
| 2017/0084060 A1* | 3/2017 | Bal | G06K 9/6272 |
| 2019/0073568 A1* | 3/2019 | He | G06V 10/40 |
| 2019/0125295 A1* | 5/2019 | Tek | A61B 8/469 |
| 2019/0130110 A1* | 5/2019 | Lee | G06F 21/57 |
| 2019/0244103 A1 | 8/2019 | Wang et al. | |
| 2020/0210773 A1* | 7/2020 | Li | G06N 3/0454 |
| 2020/0380641 A1* | 12/2020 | Higaki | G06N 3/0454 |
| 2020/0401851 A1* | 12/2020 | Mau | G06F 16/55 |
| 2021/0110522 A1* | 4/2021 | Ren | G06T 3/40 |
| 2022/0277497 A1* | 9/2022 | Patwari | G06T 11/003 |

OTHER PUBLICATIONS

Goodfellow et al., "Explaining and harnessing adversarial examples," Mar. 20, 2015, 11 pages, Cornell University.
Hawkins et al., "Predicting malignant nodules from screening CT scans," Jul. 12, 2016, pp. 2120-2128 (9 pages), vol. 11, No. 12, Journal of Thoracic Oncology.
Kim et al., "Bridging Adversarial Robustness and Gradient Interpretability," Apr. 19, 2019, 12 pages, Cornell University.
Mirsky et al., "CT-GAN: Malicious Tampering of 3D Medical Imagery using Deep Learning," Aug. 14-16, 2019, 19 pages, 28th USENIX Security Symposium, Santa Clara, CA, USA.
Paul et al., "Predicting Nodule Malignancy using a CNN Ensemble Approach," 2018, 8 pages, International Joint Conference on Neural Networks (IJCNN).
Su et al., "One Pixel Attack for Fooling Deep Neural Networks," Oct. 5, 2019,14 pages, vol. 23, No. 5, IEEE Transactions on Evolutionary Computation.
Szegedy et al, "Intriguing properties of neural networks," 10 pages, Feb. 19, 2014, Cornell University.
Tramer et al., "Ensemble adversarial training: Attacks and defenses," Apr. 26, 2020, 22 Pages, Cornell University.
Zhu et al., "Adversarial deep structured nets for mass segmentation from mammograms," Dec. 25, 2017, Cornell University.

* cited by examiner

Table 1: CNN architectures and parameters

| CNN architecture 1 | | CNN architecture 2 | | CNN architecture 3 | |
|---|---|---|---|---|---|
| Layers | Parameters | Layers | Parameters | Layers | Parameters |
| Input | 100 x100 | Input | 100 x100 | Left BRANCH | |
| Conv1 | 64x5x5,pad 0,stride 1 | Conv1 | 64x5x5,pad 0,stride 1 | Input | 100 x100 |
| Leaky ReLU | alpha=0.01 | Leaky ReLU | alpha=0.01 | Max Pool 1 | 10x10 |
| Max Pool 1 | 3x3, stride 3, pad 0 | Max Pool 1 | 3x3, stride 3, pad 0 | Dropout | 0.1 |
| Conv2 | 64x2x2,pad 0,stride 1 | Conv2 | 64x2x2,pad 0,stride 1 | Left BRANCH | |
| Leaky ReLU | alpha=0.01 | Leaky ReLU | alpha=0.01 | Conv1 | 64x5x5,pad 0,stride 1 |
| Max Pool 2 | 3x3, stride 3, pad 0 | Max Pool 2 | 3x3, stride 3, pad 0 | Leaky ReLU | alpha=0.01 |
| Dropout | 0.1 | Dropout | 0.1 | Max Pool 2 | 3x3, stride 3, pad 0 |
| FC 1+ ReLU | 128 | FC 1+ ReLU | 128 | Conv2 | 64x2x2,pad 0,stride 1 |
| FC 2+ ReLU | 8 | LSTM 1 + ReLU | 8 | Leaky ReLU | alpha=0.01 |
| L2 regularizer | 0.01 | L2 regularizer | 0.01 | Max Pool 3 | 3x3, stride 3, pad 0 |
| Dropout | 0.25 | Dropout | 0.25 | Merge Left and Right | |
| FC 3 + Sigmoid | 1 | FC 3 + Sigmoid | 1 | Conv 3 | 64x2x2, pad 0, stride 1 |
| | | | | Max Pool 4 | 2x2, stride 2, pad 0 |
| | | | | L2 regularizer | 0.01 |
| | | | | Dropout | 0.1 |
| | | | | FC 1+ Sigmoid | 1 |
| Total parameters | 841,681 | Total parameters | 845,033 | Total parameters | 39,553 |

FIG. 1

Table 2: Classification Performance of Adversarial Attacks Using Three CNNs Trained Using Seven Different Seed Points: Train On Cohort 1 Original Images Only and Test On Adversarial Cohort 2 Images

| CNN 1 | | |
|---|---|---|
| Original (no attack) | FGSM | 1-Pixel Attack |
| 75.1% | 46.4% | 72.15% |
| 73.4% | 49.4% | 71.3% |
| 74.26% | 49.4% | 71.72% |
| 74.26% | 51.5% | 71.3% |
| 75.1% | 52.74% | 70.04% |
| 73.83% | 48.1% | 71.3% |
| 73% | 39.24% | 72.5% |
| CNN 2 | | |
| Original (no attack) | FGSM | 1-Pixel Attack |
| 75.5% | 39.2% | 73% |
| 73.83% | 41.77% | 70.88% |
| 74.68% | 54% | 69.62% |
| 74.26% | 39.2% | 72.5% |
| 74.68% | 49.4% | 71.3% |
| 75.1% | 54.33% | 72.5% |
| 74.68% | 43.24% | 72.15% |
| CNN 3 | | |
| Original (no attack) | FGSM | 1-Pixel Attack |
| 76% | 39.71% | 73% |
| 75.1% | 40.56% | 71.3% |
| 76% | 37.15% | 73.4% |
| 74.26% | 37.15% | 70.04% |
| 75.5% | 39.71% | 72.5% |
| 73.83% | 36.3% | 72.15% |
| 75.5% | 40.56% | 72.5% |

FIG. 3

Table 3: Ensemble of CNNs: Train on Cohort 1 Original Images Only and Test On Adversarial Cohort 2 Images

| Approach | CNN 1: Ensemble of 7 CNNs |
|---|---|
| Original | 84.8% (0.89 AUC) |
| FGSM | 62.86% (0.41 AUC) |
| 1-Pixel Attack | 76.3% (0.77 AUC) |

| Approach | CNN 2: Ensemble of 7 CNNs |
|---|---|
| Original | 87.34% (0.89 AUC) |
| FGSM | 62.44% (0.44 AUC) |
| 1-Pixel Attack | 77.21% (0.77 AUC) |

| Approach | CNN 3: Ensemble of 7 CNNs |
|---|---|
| Original | 87.34% (0.9 AUC) |
| FGSM | 66.67% (0.53 AUC) |
| 1-Pixel Attack | 77.21% (0.82 AUC) |

| Approach | Overall: Ensemble of 7 CNNs |
|---|---|
| Original | 90.29% (0.94 AUC) |
| FGSM | 67.5% (0.5 AUC) |
| 1-Pixel Attack | 78.9% (0.84 AUC) |

FIG. 4

Table 4: Train Cohort 1 Using Original and Adversarial Images and Test on Original Cohort 2 Images

| CNN 1 | | CNN 2 | | CNN 3 | |
|---|---|---|---|---|---|
| FGSM | 1-pixel attack | FGSM | 1-pixel attack | FGSM | 1-pixel attack |
| 73% | 73% | 74.68% | 73.83% | 74.26% | 73.83% |
| 73.4% | 72.5% | 74.68% | 72.15% | 73.83% | 72.5% |
| 73.83% | 73% | 74.26% | 72.5% | 73% | 74.26% |
| 73.83% | 71.3% | 74.68% | 73.4% | 73.4% | 71.72% |
| 73.4% | 70.04% | 74.26% | 72.15% | 74.26% | 73.83% |
| 72.5% | 72.5% | 71.72% | 73% | 74.26% | 73.4% |
| 72.5% | 73% | 71.72% | 72.5% | 73.4% | 74.26% |

FIG. 5

Table 5: Ensemble of CNNs: Train Cohort 1 Using Original and Adversarial Images and Test on Original Cohort 2 Images

| Approach | CNN 1: Ensemble of 7 CNNs |
|---|---|
| FGSM | 78.05% (0.82 AUC) |
| 1-pixel attack | 77.63% (0.8 AUC) |

| Approach | CNN 2 : Ensemble of 7 CNNs |
|---|---|
| FGSM | 78.9% (0.82 AUC) |
| 1-pixel attack | 78.05% (0.82 AUC) |

| Approach | CNN 3: Ensemble of 7 CNNs |
|---|---|
| FGSM | 79.32% (0.84 AUC) |
| 1-pixel attack | 78.9% (0.82 AUC) |

| Approach | Overall : Ensemble of 21 CNNs |
|---|---|
| FGSM | 82.27% (0.88 AUC) |
| 1-pixel attack | 81.43% (0.85 AUC) |

FIG. 6

Table 6: Train Cohort 1 Using Original and Adversarial Images and Test On Adversarial Cohort 2 Images

| CNN 1 | | CNN 2 | | CNN 3 | |
|---|---|---|---|---|---|
| FGSM | 1-pixel attack | FGSM | 1-pixel attack | FGSM | 1-pixel attack |
| 68.35% | 73% | 65.77% | 73% | 70.04% | 73.4% |
| 68.35% | 71.3% | 67.5% | 70.88% | 66.24% | 72.15% |
| 67.5% | 72.5% | 66.66% | 71.72% | 65.8% | 73.83% |
| 67.08% | 71.3% | 66.66% | 73% | 69.62% | 71.72% |
| 67.5% | 70.04% | 67.93% | 72.15% | 69.19% | 73.41% |
| 67.93% | 72.5% | 67.5% | 73% | 69.19% | 73% |
| 67.93% | 73% | 67.93% | 72.5% | 68.35% | 73.41% |

FIG. 7

Table 7: Ensemble of CNNs: Train Cohort 1 On Original and Adversarial Images and Test on Adversarial Cohort 2 Images

| Approach | CNN 1: Ensemble of 7 CNNs |
|---|---|
| FGSM | 73% (0.7 AUC) |
| 1-pixel attack | 76.79% (0.79 AUC) |

| Approach | CNN 2 : Ensemble of 7 CNNs |
|---|---|
| FGSM | 72.5% (0.69 AUC) |
| 1-pixel attack | 78.05% (0.82 AUC) |

| Approach | CNN 3: Ensemble of 7 CNNs |
|---|---|
| FGSM | 74.68% (0.75 AUC) |
| 1-pixel attack | 78.5% (0.82 AUC) |

| Approach | Overall : Ensemble of 21 CNNs |
|---|---|
| FGSM | 77.63% (0.81 AUC) |
| 1-pixel attack | 80.16% (0.84 AUC) |

FIG. 8

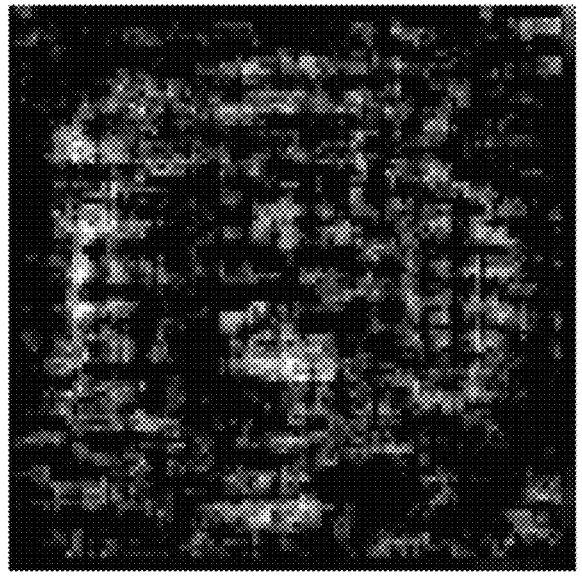 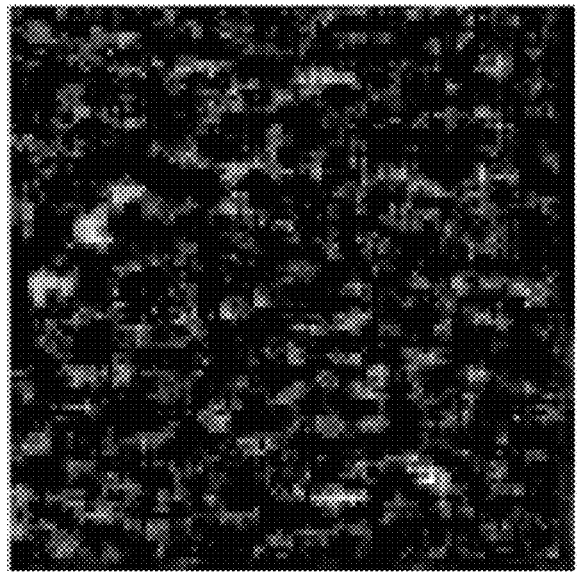
FIG. 9E
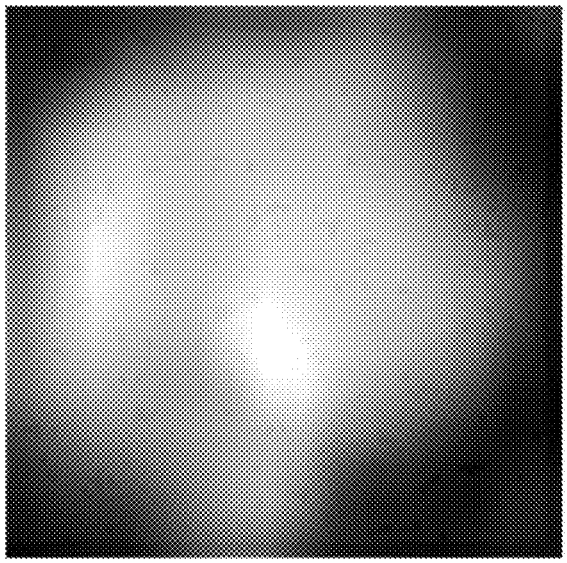 
FIG. 9F

TABLE 8

RESULTS AFTER ENSEMBLE ADVERSARIAL ATTACK – TRAIN: ORIGINAL
COHORT 1 & TEST: COHORT 2 ENSEMBLE ADVERSARIAL ATTACK

| Approach | Average | Maximum Value |
| --- | --- | --- |
| CNN 1: Ensemble of 7 CNNs | 46% (0.74 AUC) | 50.63% (0.6 AUC) |
| CNN 2: Ensemble of 7 CNNs | 41.77% (0.72 AUC) | 43% (0.64 AUC) |
| CNN 3: Ensemble of 7 CNNs | 40.1% (0.5 AUC) | 43.6% (0.52 AUC) |
| Overall: Ensemble of 21 CNNs | 46.83% (0.7 AUC) | 50.63% (0.61 AUC) |

FIG. 12

TABLE 9

RESULTS AFTER ENSEMBLE ADVERSARIAL ATTACK – TRAIN: ORIGINAL &
ADVERSARIAL COHORT 1 & TEST: COHORT 2 ORIGINAL

| Approach | Average | Maximum Value |
| --- | --- | --- |
| CNN 1: Ensemble of 7 CNNs | 75.1% (0.76 AUC) | 76.37% (0.76 AUC) |
| CNN 2: Ensemble of 7 CNNs | 76% (0.8 AUC) | 78.05% (0.82 AUC) |
| CNN 3: Ensemble of 7 CNNs | 77.2% (0.79 AUC) | 76% (0.83 AUC) |
| Overall: Ensemble of 21 CNNs | 80.2% (0.82 AUC) | 80.59% (0.82 AUC) |

FIG. 13

TABLE 10

RESULTS AFTER ENSEMBLE ADVERSARIAL ATTACK – TRAIN: ORIGINAL &
ADVERSARIAL COHORT 1 & TEST: COHORT 2 ENSEMBLE ADVERSARIAL ATTACK

| Approach | Average | Maximum Value |
| --- | --- | --- |
| CNN 1: Ensemble of 7 CNNs | 83.12% (0.83 AUC) | 81% (0.81 AUC) |
| CNN 2: Ensemble of 7 CNNs | 82.27% (0.8 AUC) | 80.16% (0.81 AUC) |
| CNN 3: Ensemble of 7 CNNs | 83.96% (0.83 AUC) | 82.27% (0.83 AUC) |
| Overall: Ensemble of 21 CNNs | 84.8% (0.86 AUC) | 83.54% (0.84 AUC) |

FIG. 14

MITIGATING ADVERSARIAL ATTACKS ON MEDICAL IMAGING UNDERSTANDING SYSTEMS

CROSS-REFERENCE TO RELATED APPLICATION

This application claims priority to U.S. provisional applications entitled, "Mitigating Adversarial Attacks on Medical Imaging Understanding Systems," having Ser. No. 62/935,179, filed Nov. 14, 2019, and "Mitigating Adversarial Attacks on Medical Imaging Understanding Systems," having Ser. No. 62/991,715, filed Mar. 19, 2020, which are both entirely incorporated herein by reference.

STATEMENT REGARDING FEDERALLY SPONSORED RESEARCH OR DEVELOPMENT

This invention was made with government support under CA143062 awarded by the National Institutes of Health. The Government has certain rights in the invention.

BACKGROUND

A deep learning system can be easily fooled by intentionally adding some noise in the image. This is called as adversarial attack.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 shows a table of parameters of various convolutional neural network (CNN) architectures in accordance with the present disclosure.

FIG. 3 shows a table of classification performance statistics of adversarial attacks using individual CNNs that are trained using original images and tested on adversarial images in accordance with embodiments of the present disclosure.

FIG. 4 shows a table of classification performance statistics of adversarial attacks using an ensemble of CNNs that are trained using original images and tested on adversarial images in accordance with embodiments of the present disclosure.

FIG. 5 shows a table of classification performance statistics of adversarial attacks using individual CNNs that are trained using original images and adversarial images and tested on original images in accordance with embodiments of the present disclosure.

FIG. 6 shows a table of classification performance statistics of adversarial attacks using an ensemble of CNNs that are trained using original images and adversarial images and tested on original images in accordance with embodiments of the present disclosure.

FIG. 7 shows a table of classification performance statistics of adversarial attacks using individual CNNs that are trained using original images and adversarial images and tested on adversarial images in accordance with embodiments of the present disclosure.

FIG. 8 shows a table of classification performance statistics of adversarial attacks using an ensemble of CNNs that are trained using original images and adversarial images and tested on adversarial images in accordance with embodiments of the present disclosure.

FIGS. 9A-9G show original images and ensemble-based adversarial images in accordance with various embodiments of the present disclosure.

FIG. 12 shows a table of classification performance statistics results of ensemble adversarial attacks using an ensemble of CNNs that are trained using original images and tested on average ensemble adversarial attack images or maximum value ensemble adversarial attack images in accordance with various embodiments of the present disclosure.

FIG. 13 shows a table of classification performance statistics results of ensemble adversarial attacks using an ensemble of CNNs that are trained using original images and average ensemble adversarial attack images or maximum value ensemble adversarial attack images and tested on original images in accordance with various embodiments of the present disclosure.

FIG. 14 shows a table of classification performance statistics results of ensemble adversarial attacks using an ensemble of CNNs that are trained using original images and average ensemble adversarial attack images or maximum value ensemble adversarial attack images and tested on average ensemble adversarial attack images or maximum value ensemble adversarial attack images in accordance with various embodiments of the present disclosure.

DETAILED DESCRIPTION

Figure 2A:
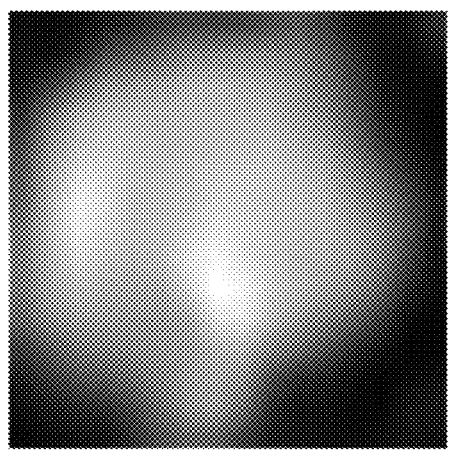
FIGS. 2A-2B show original lung nodule images in accordance with the present disclosure.
Figure 2B:
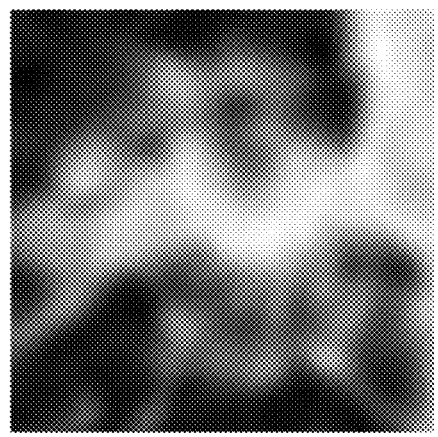
Figure 2C:
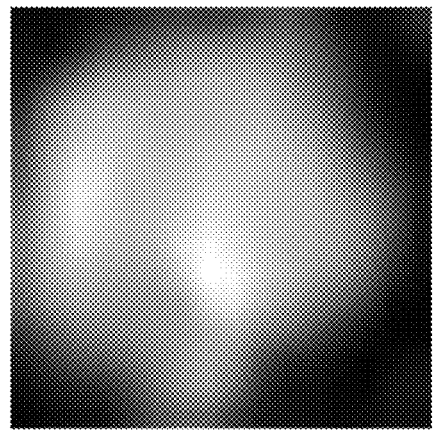
FIGS. 2C-2D show adversarial lung nodule images produced from an FGSM adversarial attack in accordance with the present disclosure.
Figure 2D:
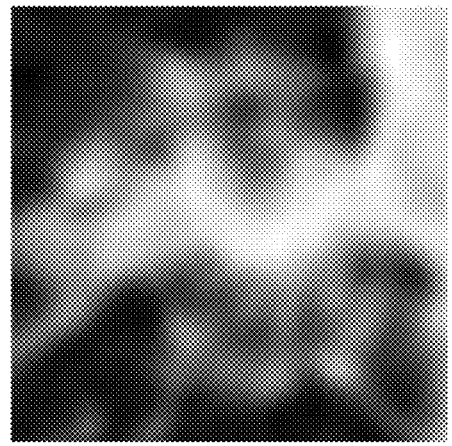
Figure 2E:
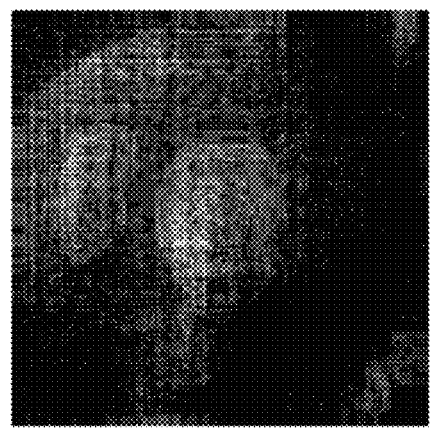
FIGS. 2E-2F show a difference between original lung nodule images and adversarial lung nodule images produced from an FGSM adversarial attack in accordance with the present disclosure.
Figure 2F:
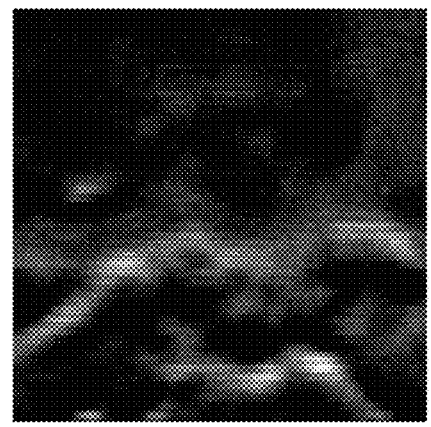
Figure 2G:
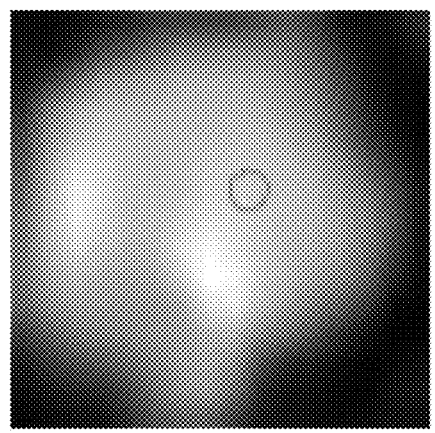
FIGS. 2G-2H show adversarial lung nodule images produced from a one pixel adversarial attack in accordance with the present disclosure.
Figure 2H:
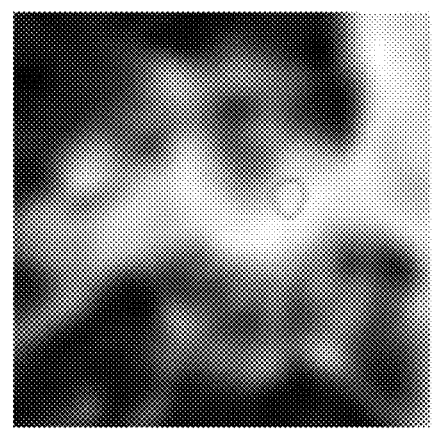

The present disclosure describes various embodiments of systems, apparatuses, and methods for a multi-initialization ensemble-based defense strategy against an adversarial attack (also referred as a multi-initialization ensemble-based analysis).

In one embodiment, an exemplary method includes training a plurality of conventional neural networks (CNNs) with a training set of images, wherein the images include original images and images modified by an adversarial attack (such as 3D images, 2D images, including 2D slices of 3D images); after training of the plurality of conventional neural networks, providing an input image to the plurality of conventional neural networks, wherein the input image has been modified by an adversarial attack; receiving a probability output for the input image from each of the plurality of conventional neural networks, wherein the probability output comprises a probability that the image belongs to one or more categories; producing an ensemble probability output for the input image by combining the probability outputs from each of the plurality of conventional neural networks; and labeling the input image as belonging to one of the one or more categories based on the ensemble probability output.

As an overview, Szegedy et al. first showed that the state-of-the-art Convolutional Neural Networks (CNN) can be fooled with a small perturbation in images. See C. Szegedy, W. Zaremba, I. Sutskever, J. Bruna, D. Erhan, I. Goodfellow, and R. Fergus, "Intriguing properties of neural networks," arXiv preprint arXiv:1312.6199, 2013. These perturbed images are called adversarial images. A recent study by Mirsky et al. showed how a person could alter a computed tomography (CT) scan by infiltrating the PACS (Picture Archiving and Communication System). See Y. Mirsky, T. Mahler, I. Shelef, and Y. Elovici, "Ct-gan: Malicious tampering of 3d medical imagery using deep learning," arXiv preprint arXiv:1901.03597, 2019. Finlayson et al. analyzed adversarial attacks on medical images using Projected Gradient Descent (PGD) and a patch-based attack. See S. G. Finlayson, H. W. Chung, I. S. Kohane, and A. L. Beam, "Adversarial attacks against medical deep learning systems," arXiv preprint arXiv:1804.05296, 2018.

Correspondingly, healthcare is a desirable and convenient target due to the vast availability of patient data through lightly secured networks. Lung cancer is the world's most frequently diagnosed cancer with a 5-year survival of 18%. To enhance the survival and patient outcome, early diagnosis of lung cancer is a priority. Computed tomography (CT) scan is the most standard imaging approach for lung cancer screening. As a result, CNN has recently been explored for cancer diagnosis.

A Convolutional Neural Network (CNN) is a variant of neural network which is using widely for image classification and recognition. The use of a Convolutional Neural Network (CNN) has grown enormously in recent years. However, the deep learned CNN may be fooled by a small amount of intentional distortion of pixel value(s). The machine learning models trained and tested on an undistorted dataset may misclassify adversarial images. These distorted images can also deceive human recognition. Intentional pixel distortion can also be applied to CT scans of lung nodules and may also impact the malignancy prediction.

In accordance with various embodiments of the present disclosure, a multi-initialization CNN ensemble approach can be utilized to enhance correct malignancy prediction on both original and adversarial attack examples. In one embodiment, adversarial images can be added in the training set to reduce the rate of misclassification and make the CNN models more robust to an adversarial attack. In an exemplary implementation, an improved CNN ensemble defense strategy was applied using multiple CNNs to enhance the classification performance and robustness of an individual CNN architecture. As an example, 21 outputs obtained from 3 CNNs after training using seven initializations are averaged to produce an ensemble pseudo probability output.

As a non-limiting example, the present disclosure considers the problem of an adversarial attack on medical images with an application to lung nodule malignancy prediction. Such an adversarial attack can cause significant changes in lung nodule malignancy prediction accuracy. Accordingly, untargeted adversarial attacks, such as the fast gradient signed method (FGSM) and one-pixel attack, are investigated that could be easily performed after generation of CT scans and would not need to add or remove any portion of a tumor on the CT scans. While these types of changes would be indiscernible to a physician's eyes, they can still mislead a CNN.

The fast gradient signed method (FGSM) is one of the first and influential adversarial attacks proposed by Goodfellow et al. See I. J. Goodfellow, J. Shlens, and C. Szegedy, "Explaining and harnessing adversarial examples," arXiv preprint arXiv:1412.6572, 2014. The FGSM utilizes the gradient of the loss of an input image to generate an adversarial image maximizing the loss. The FGSM approach can be summarized as, $$advI = I + \epsilon * sign(\nabla_I * J(\theta, I, Y)) \quad (1)$$

where advI is the adversarial image, I is the original Image, Y is the image label, $\epsilon$ is the amount of perturbation to be added, $\theta$ is the CNN parameters, and J is the loss function.

Regarding the One-Pixel Attack, Su et al. experimented with altering different numbers of pixels and showed that with a change of just one pixel, the CNN prediction could be altered. See J. Su, D. V. Vargas, and K. Sakurai, "One pixel attack for fooling deep neural networks," IEEE Transactions on Evolutionary Computation, 2019. The differential Evolution (DE) algorithm is an evolutionary algorithm, which was used to choose one pixel iteratively. At first, by modifying a random pixel, several adversarial images are generated and then a CNN model is used to check the prediction. Then, by combining the position of the pixels from the previous stage and colors, more adversarial images are generated and again a CNN model is used to analyze the prediction. Now for any pixel that lowered the CNNs prediction from the first step, those pixels are replaced with the current value and repeat for a few iterations. After the final iteration, the pixel value that most changed the CNNs prediction will be returned as the attack image.

Researchers have previously proposed various defense strategies to boost the robustness of a CNN model against an adversarial attack. For example, Goodfellow et al. added adversarial examples in the training set to improve the classification performance for the MNIST dataset. See I. J. Goodfellow, J. Shlens, and C. Szegedy, "Explaining and harnessing adversarial examples," arXiv preprint arXiv: 1412.6572, 2014. Tramer et al. proposed an ensemble adversarial training approach with a single classifier, not a traditional multiple classifier predictor. See F. Tramer, A. Kurakin, N. Papernot, I. Goodfellow, D. Boneh, and P. McDaniel, "Ensemble adversarial training: Attacks and defenses," arXiv preprint arXiv:1705.07204, 2017. They incorporate adversarial samples for training from different CNN's to enhance the diversity and robustness.

In accordance with the present disclosure, various embodiments of an exemplary defense strategy combine adversarial examples in the training set and enhance classification performance by creating an ensemble of CNNs.

In various embodiments, three CNN architectures (referred as CNN architecture 1, 2, and 3) are designed using Keras and Tensorflow. RMSprop optimizer was chosen to train the CNNs with a learning rate of 0.0001 and a batch size of 16. Each of the CNNs was trained for 200 epochs. Overfitting is very common for a CNN. To reduce overfitting dropout along with L2 normalization was applied before the final classification layer. In the final classification layer, the sigmoid activation was used as there are 2 classes (incident lung cancer and control cases). The parameters of the CNN architectures are shown in Table 1 of FIG. 1. Detailed analysis of the CNN architectures and parameters can be found in a paper by R. Paul, S. Hawkins, M. B. Schabath, R. J. Gillies, L. O. Hall, and D. B. Goldgof, titled "Predicting malignant nodules by fusing deep features with classical radiomics features," Journal of Medical Imaging, vol. 5, no. 1, p. 011021, 2018.

From the National Cancer Institutes (NCI) cancer data access system, a de-identified subset of malignant and control cases from the CT arm of the National Lung Screening Trial (NLST) was selected for use in an embodiment of the present disclosure. The National Lung Screening Trial (NLST) was a multiinstitutional study spanning three years. In the first year, there was a baseline scan (T0) and two follow-up scans (T1 and T2) in the next two years with a one-year gap. An exemplary analysis was conducted with the CT scans from the baseline scan (T0). These cases from the baseline scan was divided into two Cohorts: Cohort 1 (training set) and Cohort 2 (test set) and each cohort had two classes: incident lung cancer and control cases. Cohort 1 included cases which had a positively screened nodule during the baseline scan (T0) and after the first follow-up scan (T1) some of these positively screened nodules were found to be malignant. Cohort 1 had 85 incident lung cancer and 176 control cases. Cohort 2 included cases where some of the positively screened nodules from the baseline scan (T0) were found to be malignant after the second follow-up scan (T2), i.e. approximately two years after the baseline scan. Cohort 2 had 85 incident lung cancer and 152 control cases. Details about the selection of Cohorts can be found in a paper by S. Hawkins, H. Wang, Y. Liu, A. Garcia, O. Stringfield, H. Krewer, Q. Li, D. Cherezov, R. A. Gatenby, Y. Balagurunathan et al., titled "Predicting malignant nodules from screening CT scans," Journal of Thoracic Oncology, vol. 11, no. 12, pp. 2120-2128, 2016.

Definiens Software was used by a radiologist with more than 9 years of experience to segment the nodules from the CT scans. With a two-dimensional CNN, a slice with the largest nodule area was chosen for each patient. Then, only the nodule region was extracted from the slice. For experimental analysis and results, Cohort 1 and Cohort 2 were chosen as the training set and test set, respectively. Cohort 1 randomly was divided into training (70%) and validation set (remaining 30%). Next, a rotation of 12-degrees and vertical flipping were applied on both training and validation. Cohort 2 was kept completely separate for final model evaluation using accuracy and area under the receiver-operator curve (AUCROC).

A classification performance of 75.1% (0.84 AUC), 75.5% (0.86 AUC), and 76% (0.87 AUC) accuracy was achieved using CNN architecture 1, 2, and 3, respectively without adversarial attack. Results obtained after the adversarial attack were compared with the original results, in which FGSM (epsilon=0.01) and a one-pixel attack were carried out on the lung nodule images. CNN architecture 1 was used to generate the attack images. Examples of adversarial attack images are shown in FIGS. 2A-2H. The attack was performed only on Cohort 2 which was an unseen dataset.

A CNN model trained on Cohort 1 (no adversarial attack was performed on Cohort 1) was tested on Cohort 2 (adversarial attack was performed here). As such, FGSM attack images were generated for Cohort 2. We obtained 46.4% (0.38 AUC), 39.24% (0.36 AUC), and 39.71% (0.42 AUC) classification accuracy using CNN architecture 1, 2 and 3, respectively. This resulted in a 28%, 36%, and 36% decrease in classification accuracy using CNN architecture 1, 2 and 3, respectively. Using the DE (Differential Evolution) algorithm, one-pixel attack images for only Cohort 2 were obtained. For the DE algorithm, five iterations were used. We observed 72.15% (0.7 AUC), 73% (0.69 AUC) and 73% (0.72 AUC) classification accuracy using CNN architecture 1, 2, and 3, respectively. For the one-pixel attack, the accuracy did not drop much, which indicates that the exemplary CNNs were less affected by a one pixel change.

For defending against adversarial attacks, each of the exemplary CNN architectures were trained multiple times (e.g., seven) with different seed point initializations to verify the adversarial attacks stability and the performance variability. An ensemble defense strategy was applied using multiple CNNs to enhance the classification performance and robustness of individual CNN architecture. For comparison, the performance of CNNs on original Cohort 2 images was analyzed. Detailed results obtained from 3 CNNs after training using seven initializations are shown in Table 2 of FIG. 3. Then, an ensemble was produced by averaging the pseudo probability output from 21 CNNs (3 CNNs with 7 different seed points). An improvement against the adversarial attacks was observed. Using the ensemble, 67.51% classification accuracy was obtained which was a 12-25% improvement from the results shown in Table 3 of FIG. 4.

Then, the stability of the adversarial attack and the variability of the CNNs classification performance was analyzed for the one-pixel attack. Detailed results obtained from 3 CNNs after training using seven initializations are shown in Table 2 (FIG. 3). Then, an ensemble was produced by averaging the pseudo probability output from 21 CNNs (3 CNNs with 7 different seed points). 78.9% accuracy was achieved using the ensemble, which was an improvement on the results shown in Table 2 (FIG. 3). The ensemble results are shown in Table 3 (FIG. 4).

In one embodiment, adversarial images (both FGSM and one-pixel attack) were generated for Cohort 1. Then, the Cohort 1 adversarial images were divided into 70% training and 30% validation and the data augmentation was performed as mentioned earlier. Next, the adversarial images were added to the original images of Cohort 1. CNN training was performed on the enhanced Cohort 1 dataset. Now, the retrained CNNs were tested separately on original Cohort 2 images and adversarial Cohort 2 images. This analysis was conducted to check how much reduction (for Cohort 2 original images) or improvement of performance (for Cohort 2 adversarial images) was achieved. For FGSM, after training on an enhanced training set and testing on original Cohort 2 nodules images, the performance of classification for all CNNs was reduced by 2-3%. Whereas an improvement in classification accuracy of 15-20% was observed after testing on adversarial Cohort 2. Detailed results are shown in Table 4 of FIG. 5 and Table 5 of FIG. 6.

For the one-pixel attack, after training on the enhanced training set and testing on original Cohort 2 nodules images, the performance of classification for all CNNs was reduced by 2-4%. Whereas an improvement in classification accuracy of 1-3% was observed after testing on adversarial Cohort 2. Detailed results are shown in Table 6 of FIG. 7 and Table 7 of FIG. 8.

The results with adversarial images in training plus an ensemble of classifiers is more accurate than a single classifier on clean data. However, the results are 13% less accurate than an ensemble on clean data for FGSM and 10% less accurate for a single pixel attack. Still, the results are a big improvement over the 30% plus drop from FGSM seen without mounting a defense in accordance with embodiments of the present disclosure.

In accordance with various embodiments of the present disclosure, the problem of an adversarial attack on medical images is addressed with an application to lung nodule malignancy prediction. Accordingly, an ensemble-based defense strategy has been developed that reduces the effect of an adversarial attack that utilizes an exemplary multi-initialization based CNN ensemble. For example, in one embodiment, each of multiple CNN architectures are trained using different initializations, and from each CNN, a pseudo probability is obtained to produce an ensemble pseudo probability by averaging that improves malignancy prediction. In various embodiments, training can be improved by adding adversarial images in the training set, which can reduce a rate of misclassification and make the CNN models more robust to an adversarial attack.

Based on the success of an ensemble strategy for defense against the adversarial attack, an exemplary ensemble-based adversarial attack is employed in various embodiments. In one embodiment, an FGSM attack was chosen for the ensemble adversarial attack as it showed more reduction in the classification performance. The classification performance of the CNNs varied as CNNs were trained using different initializations. For example, a CNN using architecture 1 trained using seven initializations generates seven sets of adversarial images. Two ensemble strategies (Averaging and maximum value) may then be used to merge these seven sets of images. For the averaging approach, all the seven images are combined using the average value per pixel location to generate a single image. Similarly, for the maximum value approach, the seven images are combined using the maximum values per pixel location to generate a single image.

Figure 9A:
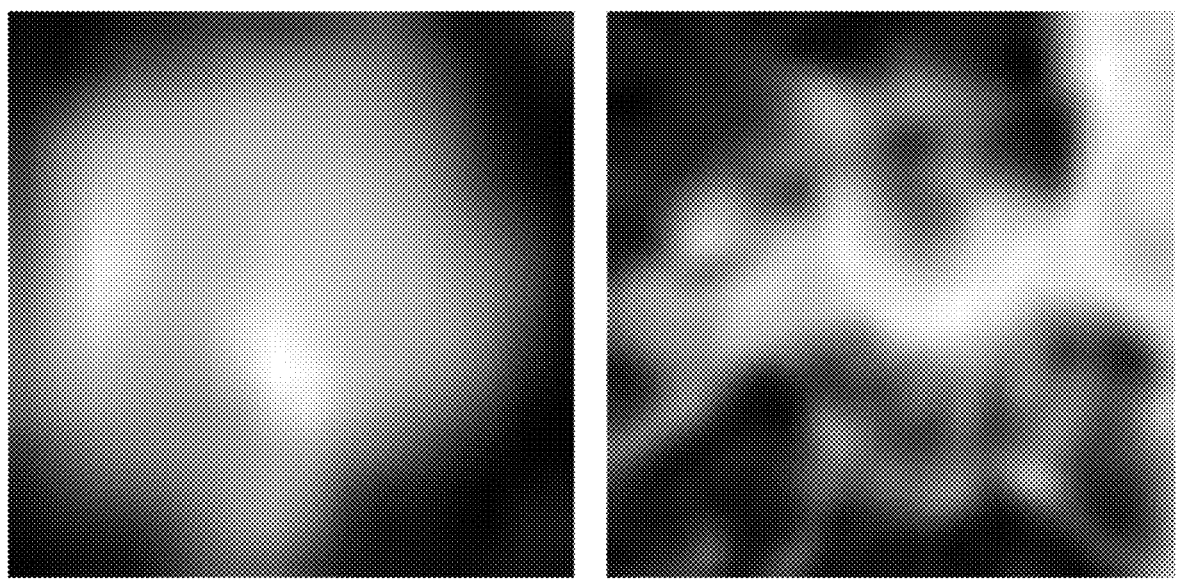
Figure 9B:
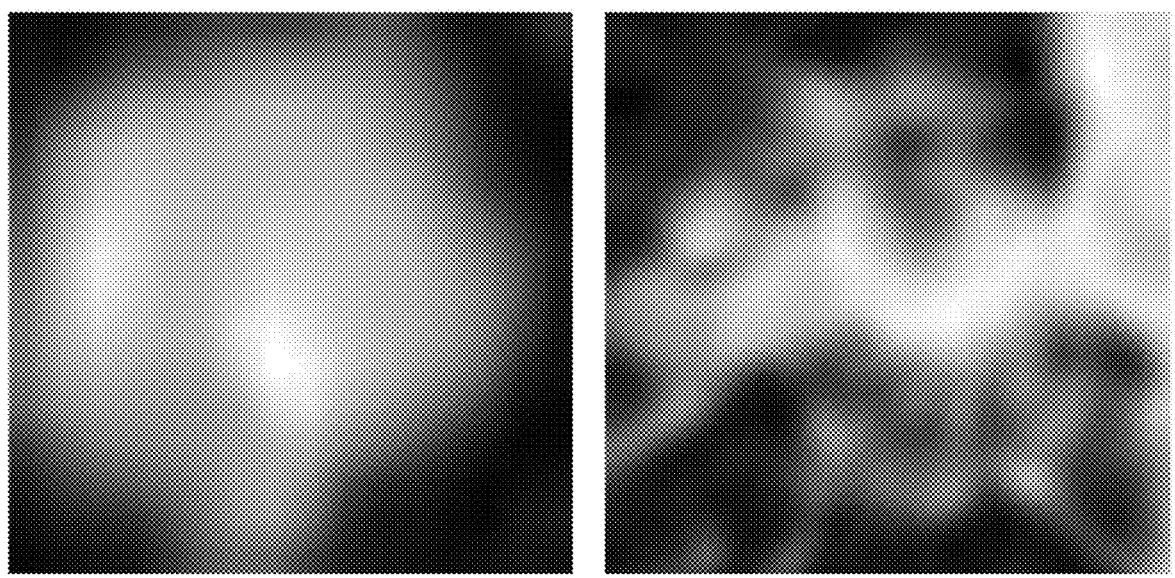
Figure 9C:
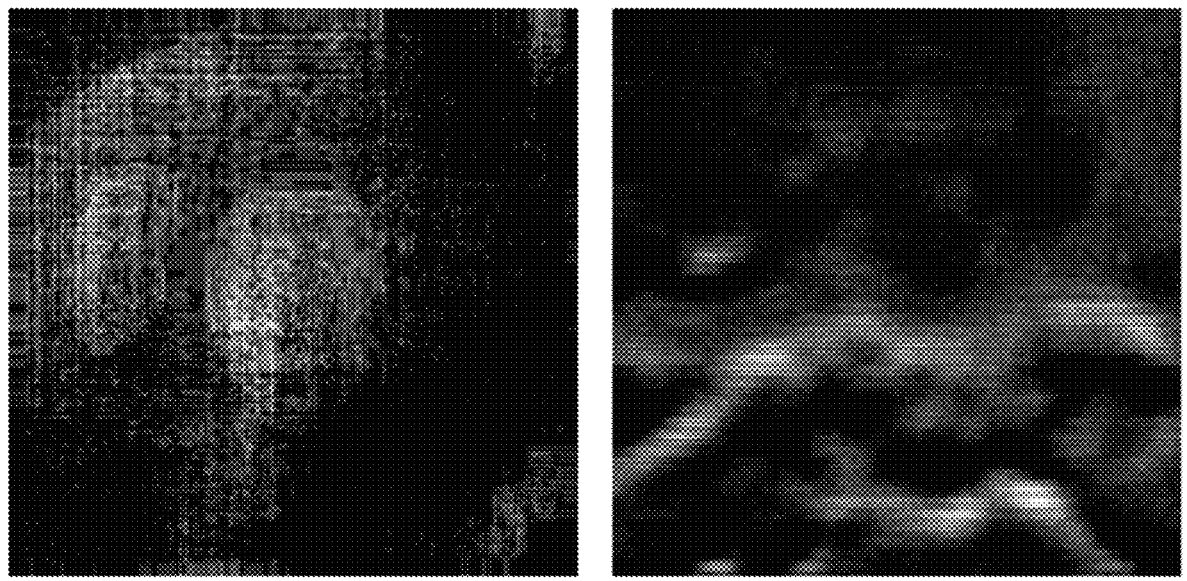
Figure 9D:
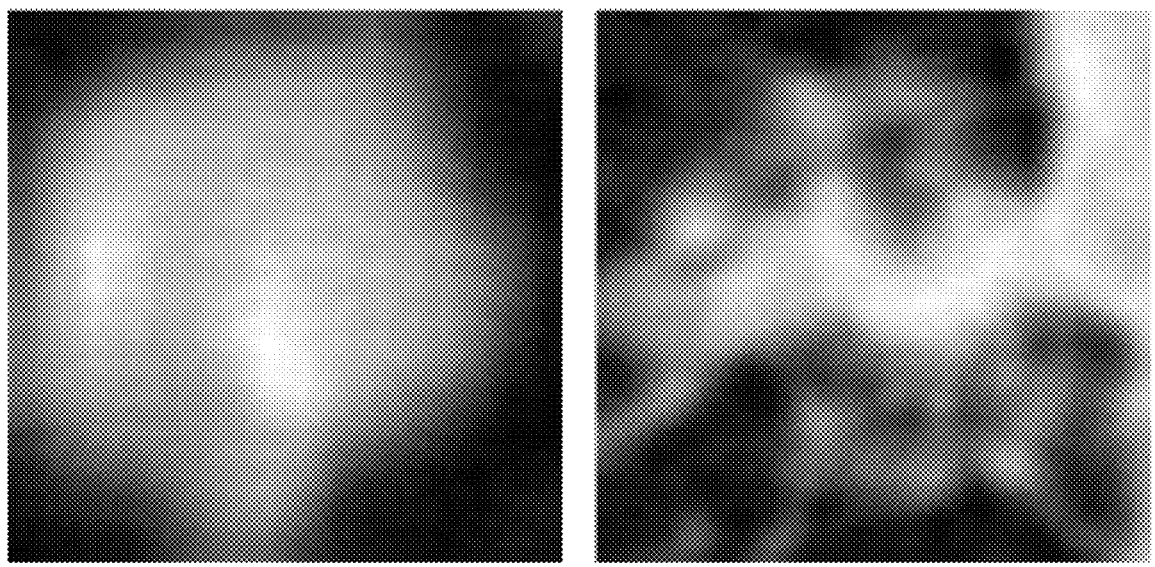
Figure 9G:
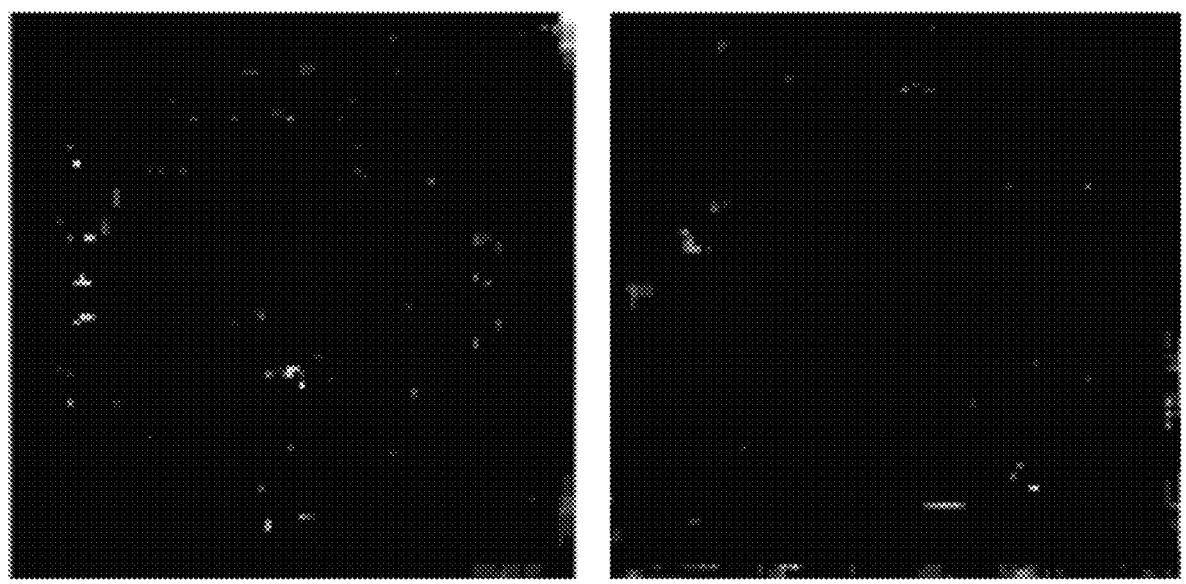

FIGS. 9A-9G show the ensemble-based adversarial images, in one embodiment. In particular, FIG. 9A shows two original images. FIG. 9B shows FGSM adversarial images corresponding to the two original images. FIG. 9C shows the difference between the original images and the FGSM adversarial images. FIG. 9D shows ensemble-based adversarial images based on the averaging approach. FIG. 9E shows the difference between the original images and the ensemble-based adversarial images based on the averaging approach. FIG. 9F shows the ensemble-based adversarial images based on the maximum value approach. FIG. 9G shows the difference between the original images and the ensemble-based adversarial images based on the maximum value approach.

The maximum value ensemble image was found to have very few pixel value variations as compared to the original image. Previous experiments were performed over these ensemble adversarial images as well to check if they could produce more reduction in classification performance than the single adversarial attack.

For a discussion of an exemplary implementation of the Ensemble Adversarial Attack by Averaging strategy, an adversarial ensemble attack was generated for Cohort 2 data only, in which we tested our models (trained CNN models on original Cohort 1) on the new adversarial images of Cohort 2. After utilizing seven initializations, CNN 1, 2, and 3 achieved the maximum accuracy of 52.23%, 53.2%, and 37.97%, respectively, and the minimum accuracy of 39.6%, 37.97%, and 36.28%, respectively. The results were very diversified, and we found that the accuracy of our classification was reduced from the original FGSM results shown in FIGS. 10A-10D by 1%, 1%, and 3% respectively for CNN 1, 2, and 3.

Figure 10A:
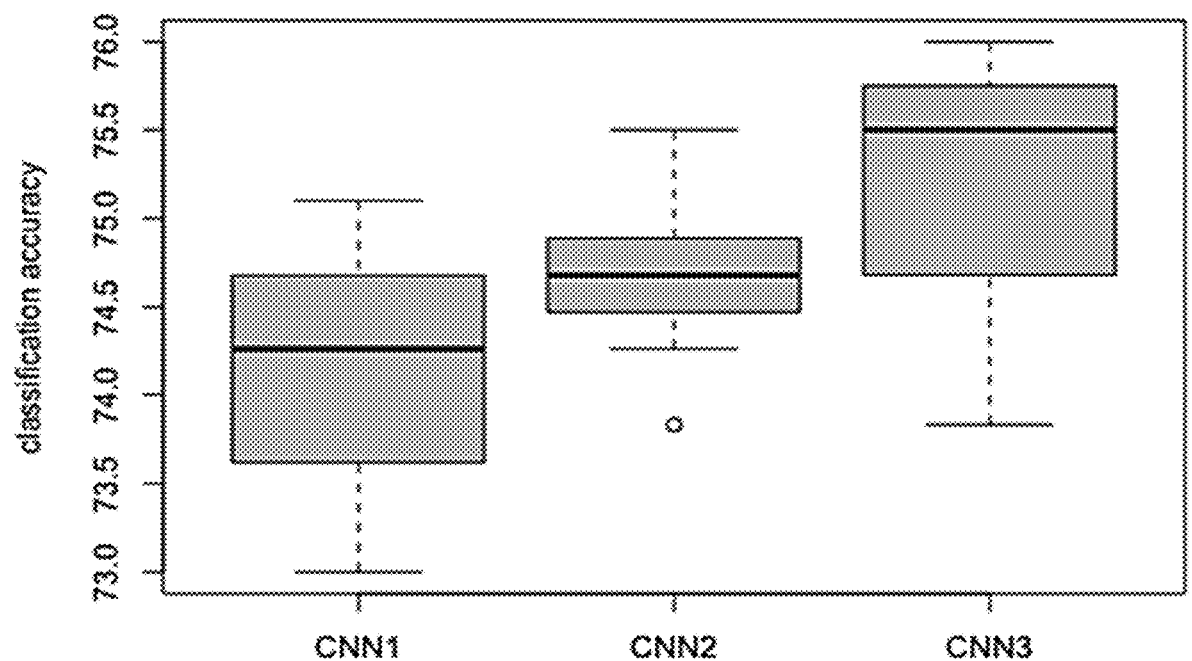
FIGS. 10A-10D show box plots of classification accuracy variations for a plurality of CNNs using various combinations of original and adversarial attack images during training and testing in accordance with various embodiments of the present disclosure.
Figure 10B:
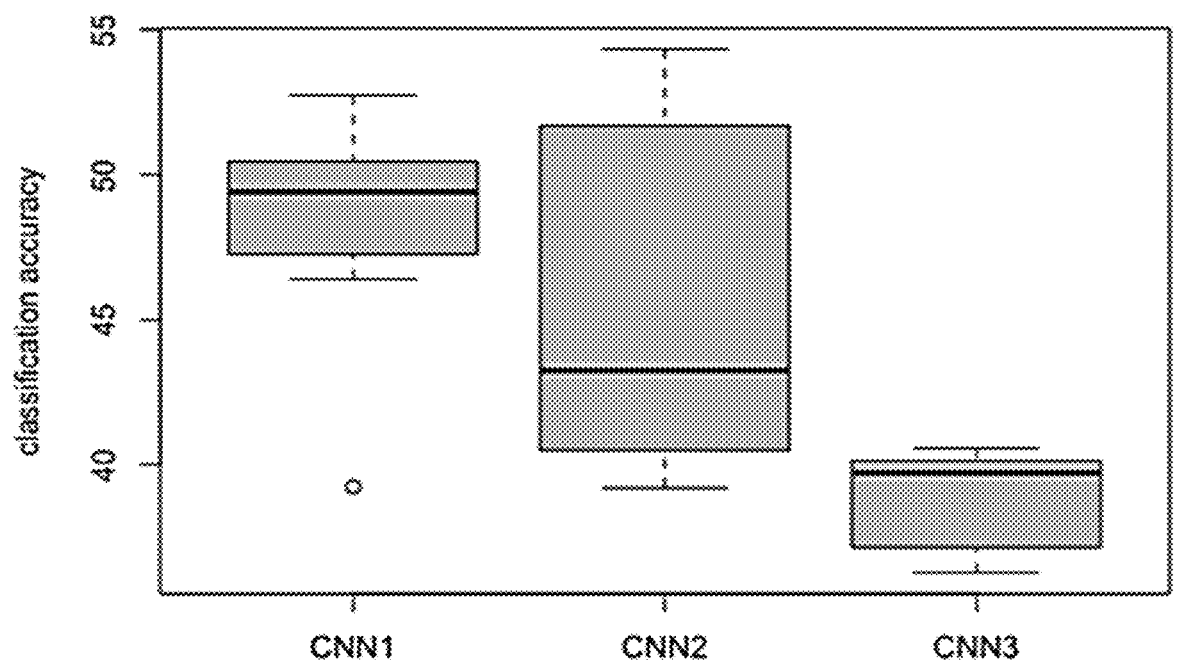
Figure 10C:
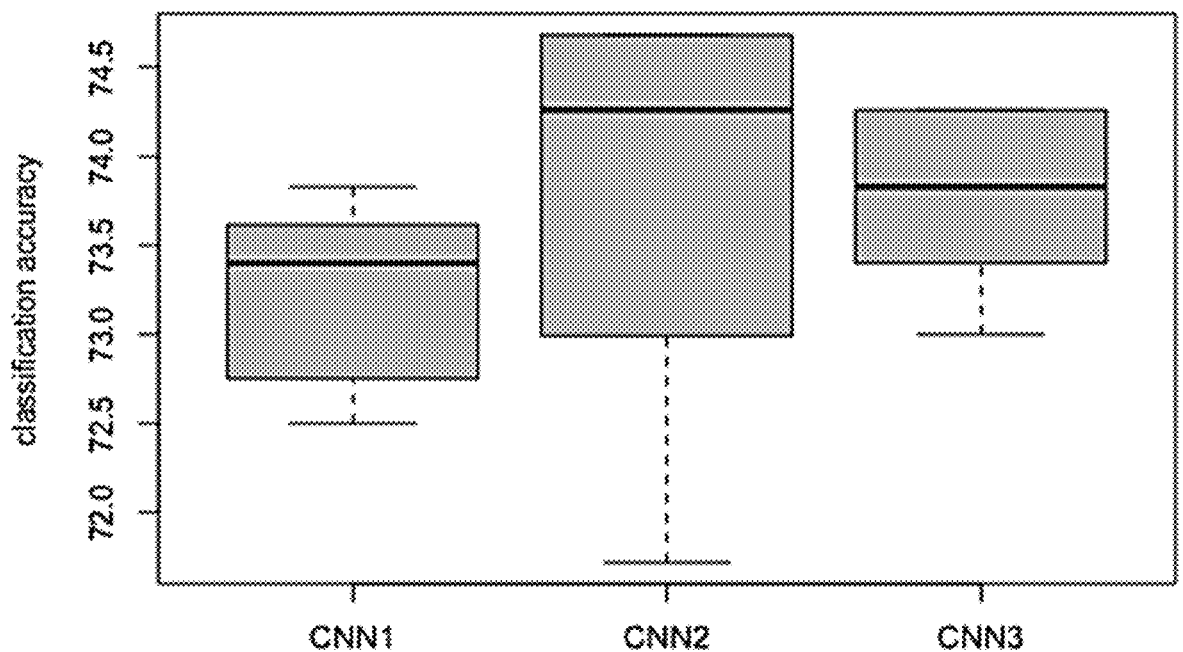
Figure 10D:
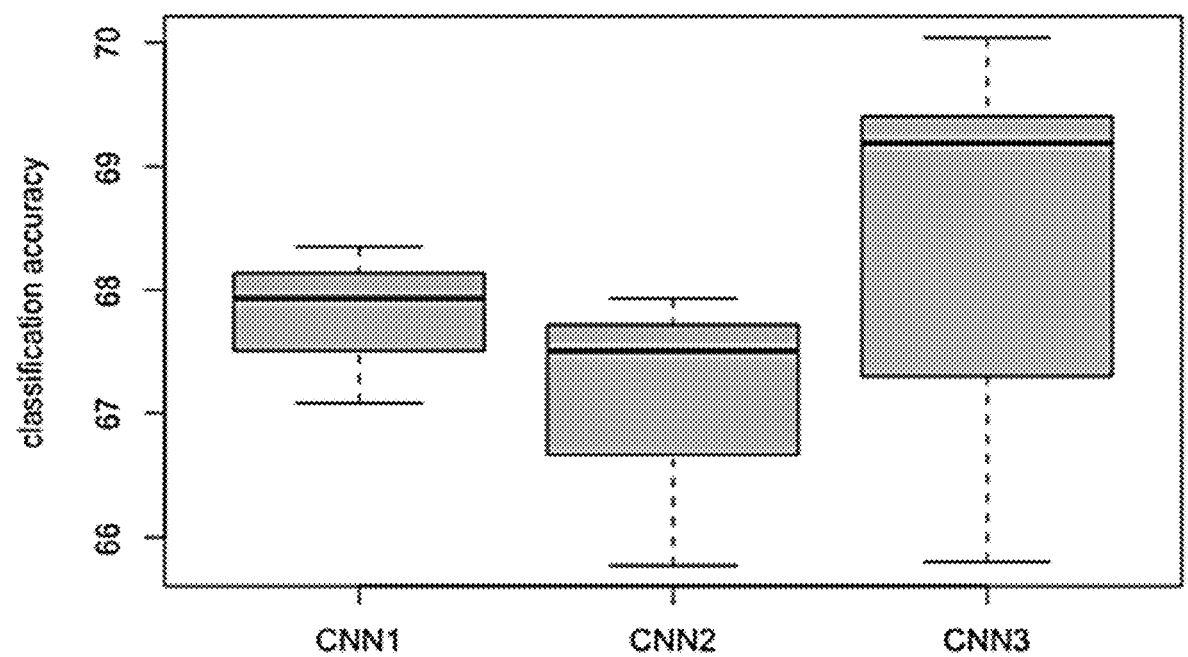
Figure 11A:
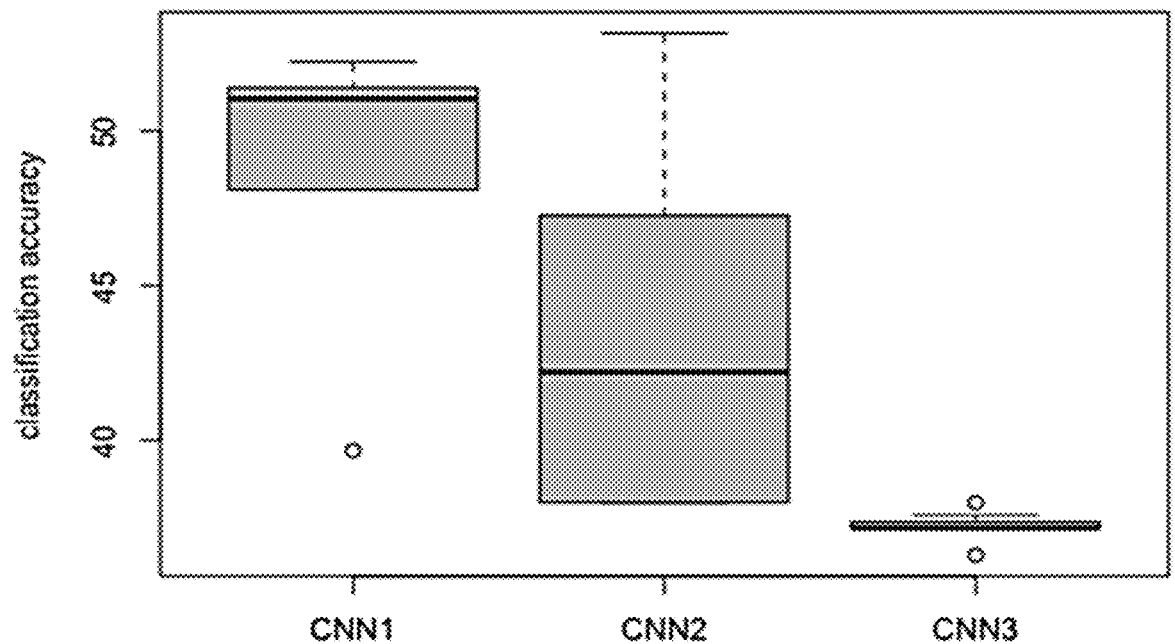
FIGS. 11A-11B show box plots of classification accuracy variations for a plurality of CNNs using original images during training and average ensemble adversarial attack images or maximum value ensemble adversarial attack images during testing in accordance with various embodiments of the present disclosure.
Figure 11B:
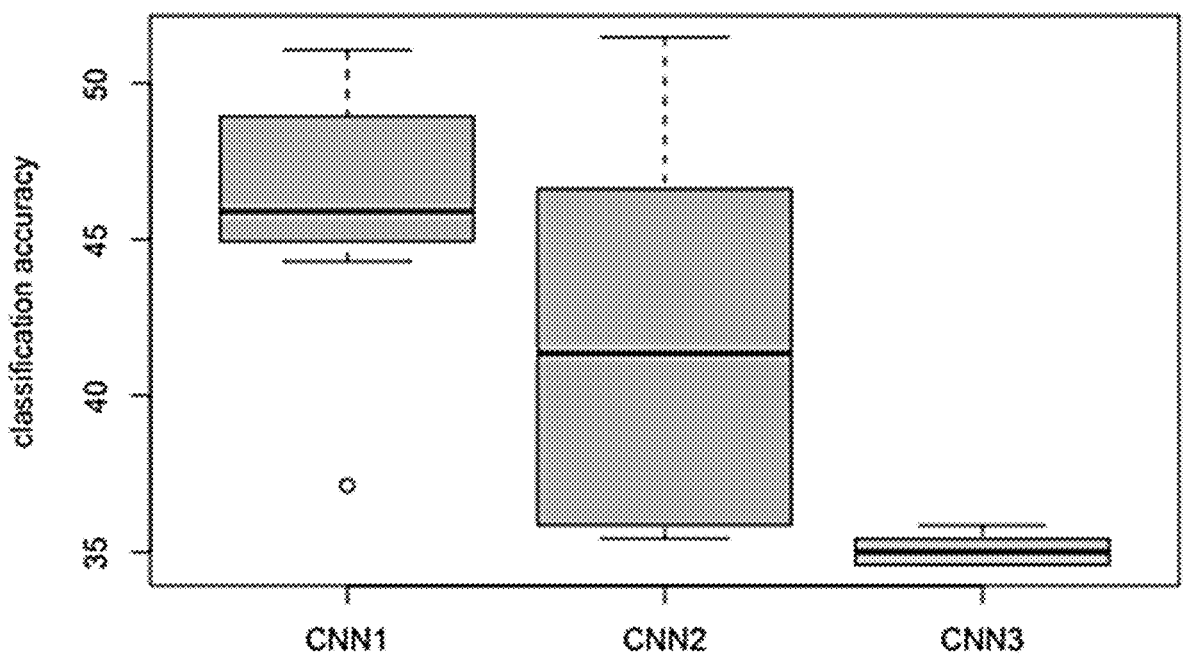

FIGS. 10A-10D shows box plots of variations for each CNN for original and adversarial attack. FIG. 10A shows classification accuracy for CNN 1, 2, and 3 for original images without any adversarial attack. FIG. 10B shows classification accuracy for CNN 1, 2, and 3 after training on original Cohort 1 images and testing on adversarial Cohort 2 images. FIG. 10C shows classification accuracy for CNN 1, 2, and 3 after training on original and adversarial Cohort 1 images and testing on original Cohort 2 images. FIG. 10D shows classification accuracy for CNN 1, 2, and 3 after training on original and adversarial Cohort 1 images and testing on adversarial Cohort 2 images. FIGS. 11A-11B display detailed results. In particular, FIG. 11A shows the classification accuracy for CNN 1, 2, and 3 after training on original Cohort 1 images and testing on average ensemble adversarial Cohort 2 images. FIG. 11B shows the classification accuracy for CNN 1, 2, and 3 after training on original Cohort 1 images and testing on maximum value ensemble adversarial Cohort 2 images.

An ensemble of 21 CNNs (3 CNNs with seven initialization) was created and obtained 46.83% accuracy with 0.7 AUC. During testing, the FGSM attack was carried out only on Cohort 1, and the adversarial data was added to the original Cohort 1 data. Each CNN was trained on this enhanced data and tested on both original and average ensemble adversarial data of Cohort 2. After training on the improved Cohort 1 and testing on original Cohort 2, we noticed that classification accuracy for all CNNs had been decreased by 3-5%. Then an ensemble of 21 CNNs was made, and 80.2% accuracy (0.82 AUC) was achieved. Detailed results are shown in Table 8 of FIG. 12, Table 9 of FIG. 13, and Table 10 of FIG. 14 and FIGS. 15A-15D.

Figure 15A:
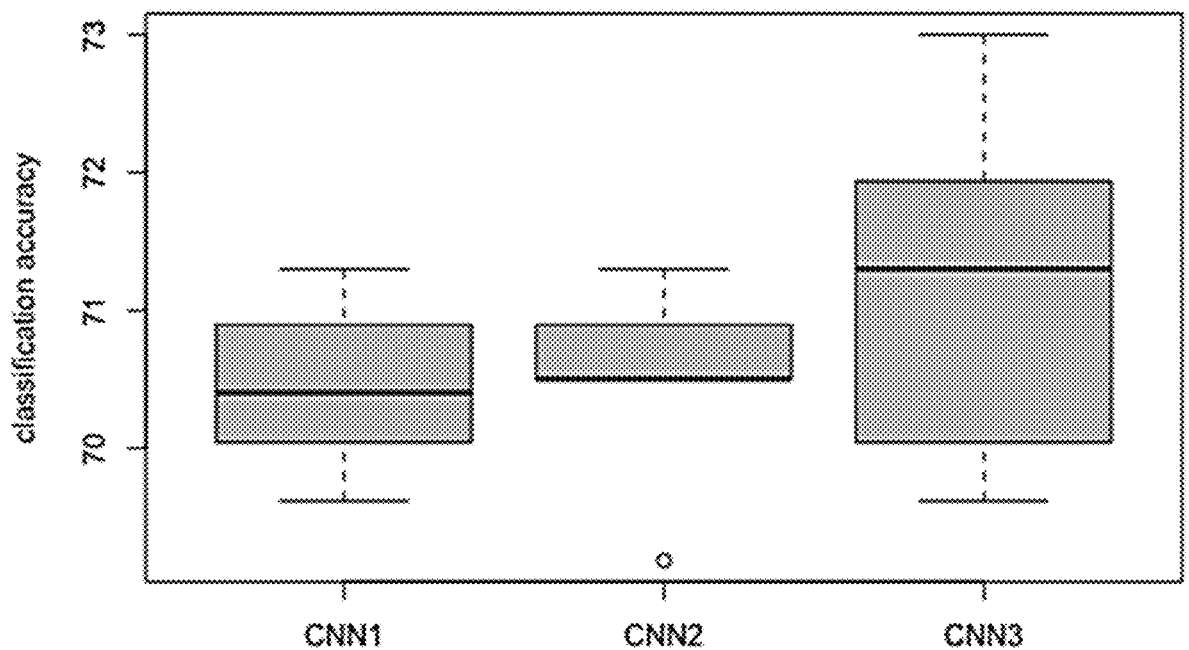
FIGS. 15A-15D show box plots of classification accuracy variations for a plurality of CNNs using original and average ensemble adversarial attack images or original and maximum value ensemble adversarial attack images during training and original, average ensemble adversarial attack images, or maximum value ensemble adversarial attack images during testing in accordance with embodiments of the present disclosure.
Figure 15B:
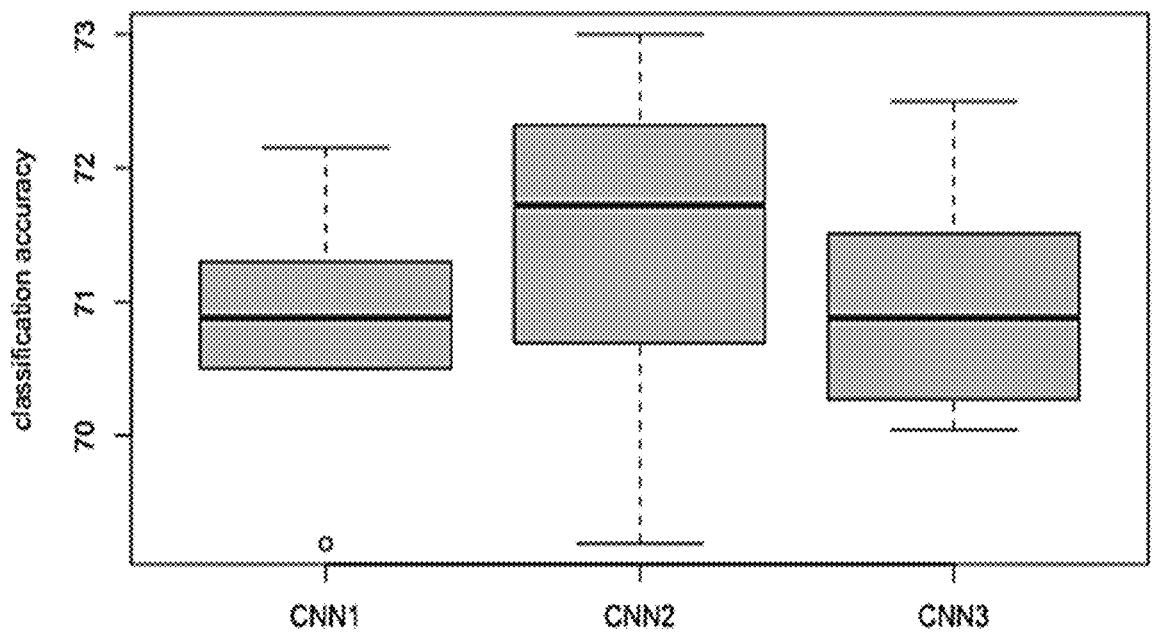
Figure 15C:
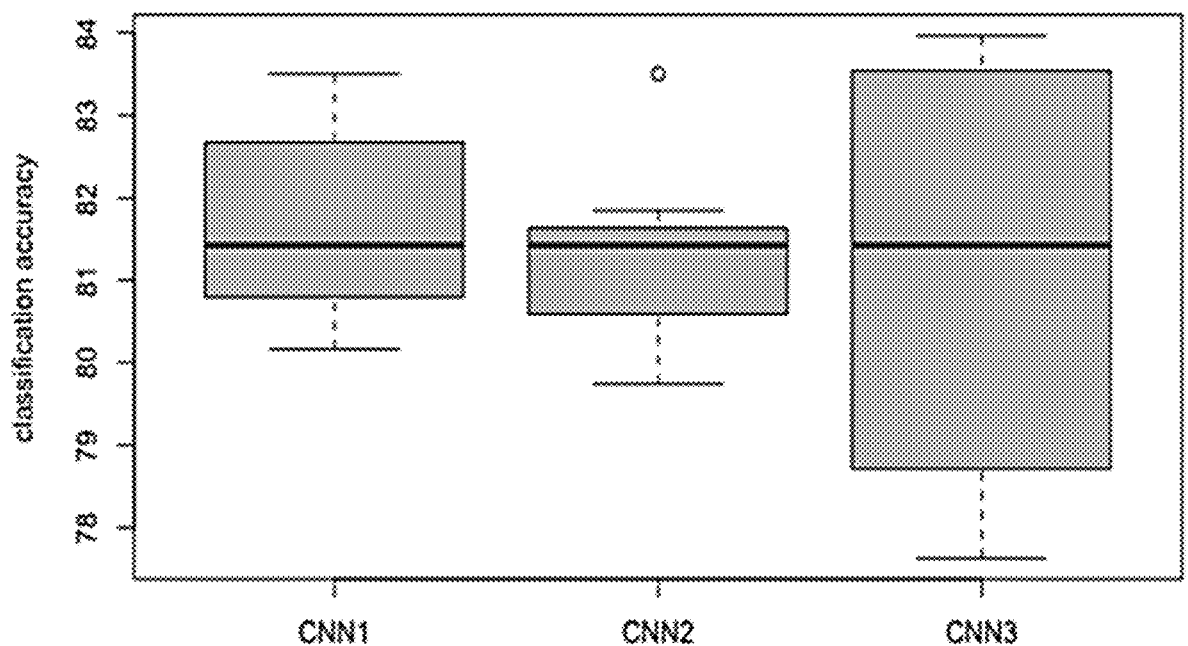
Figure 15D:
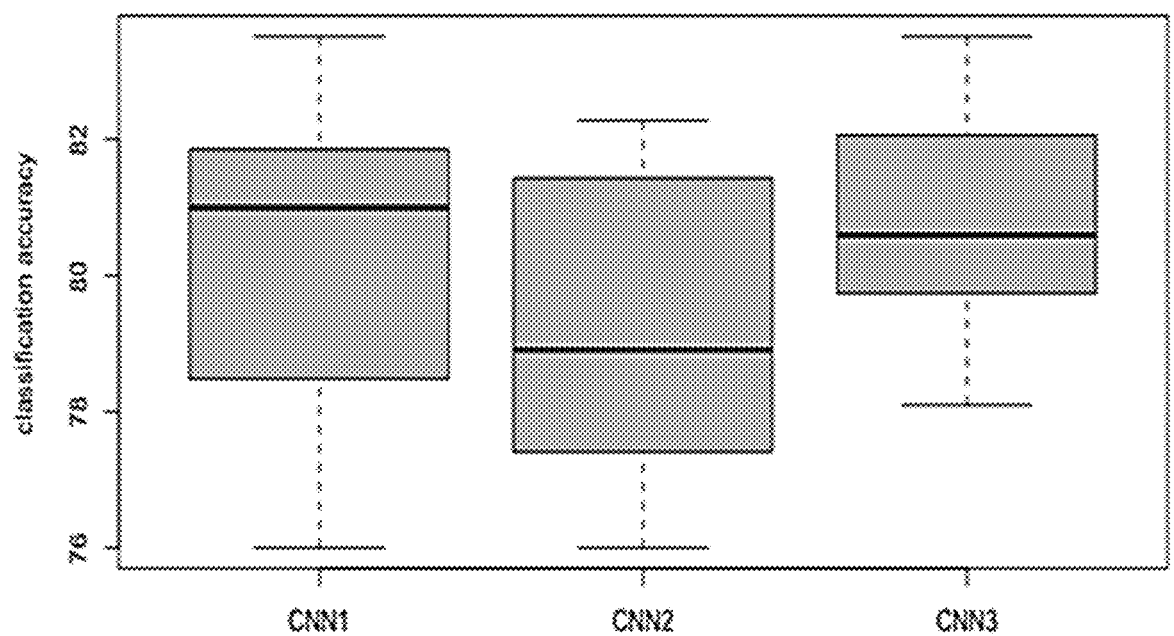

In particular, FIGS. 15A-15D show box plots of variations for each CNN after a defense against an ensemble adversarial attack. FIG. 15A shows classification accuracy for CNN 1, 2, and 3 after training on original and average ensemble adversarial Cohort 1 images and testing on original Cohort 2 images. FIG. 15B shows classification accuracy for CNN 1, 2, and 3 after training on original and maximum value ensemble adversarial Cohort 1 images and testing on original Cohort 2 images. FIG. 15C shows classification accuracy for CNN 1, 2, and 3 after training on original and average ensemble adversarial Cohort 1 images and testing on average ensemble Cohort 2 images. FIG. 15D shows classification accuracy for CNN 1, 2, and 3 after training on original and maximum value ensemble adversarial Cohort 1 images and testing on maximum value ensemble Cohort 2 images.

For testing of the Ensemble Adversarial Attack by Maximum value strategy, we generated an ensemble maximum value adversarial attack on the Cohort 2 data only. We applied our models (trained CNN models on original Cohort 1) on the new adversarial images of Cohort 2. After utilizing seven initializations, CNN 1, 2, and 3 achieved the maximum accuracy of 51.05%, 51.5%, and 35.86%, respectively, and the minimum accuracy of 37.13%, 35.44%, and 34.59%, respectively. We observed that the accuracy of our classification was reduced from the original FGSM results shown in FIGS. 10A-10D by 2%, 3%, and 5%, respectively, for CNN 1, 2, and 3. A maximum value-based ensemble attack generated more reduction in classification accuracy than average based ensemble attack and single FGSM attack. FIGS. 11A-11B displays detailed results.

An ensemble of 21 CNNs (3 CNNs with seven initializations) was created and obtained 50.63% accuracy with 0.61 AUC. Now, the FGSM attack was carried out only on Cohort 1, and the adversarial data was added to the original Cohort 1 data. Each CNN was trained on this enhanced data and tested on both original and maximum value ensemble adversarial data of Cohort 2. After training on the enhanced Cohort 1 and testing on original Cohort 2, we noticed that classification accuracy for all CNNs had been decreased by 3-6%. Then an ensemble of 21 CNNs was developed, and 80.6% accuracy (0.82 AUC) was accomplished. Detailed results are shown in Tables 8, 9, and 10 (in FIGS. 12-14) and FIGS. 15A-15D.

An overview of various concepts and embodiments for systems, apparatuses, and methods of the present disclosure are described in the following paper which is included as an appendix and is incorporated herein in its entirety: "Ensemble Adversarial Attack and Defense Against Medical Deep Learning System."

In accordance with embodiments of the present disclosure, an ensemble of multiple adversarial images using averaging and maximum value showed more reduction in classification analysis than a single FGSM image. The maximum value-based ensemble adversarial attack showed the highest reduction in classification performance and also showed the lowest change in pixel value. We also discovered that the classification performance would be enhanced by including adversarial images in the training set and creating a multi-initialization ensemble.

Figure 16:
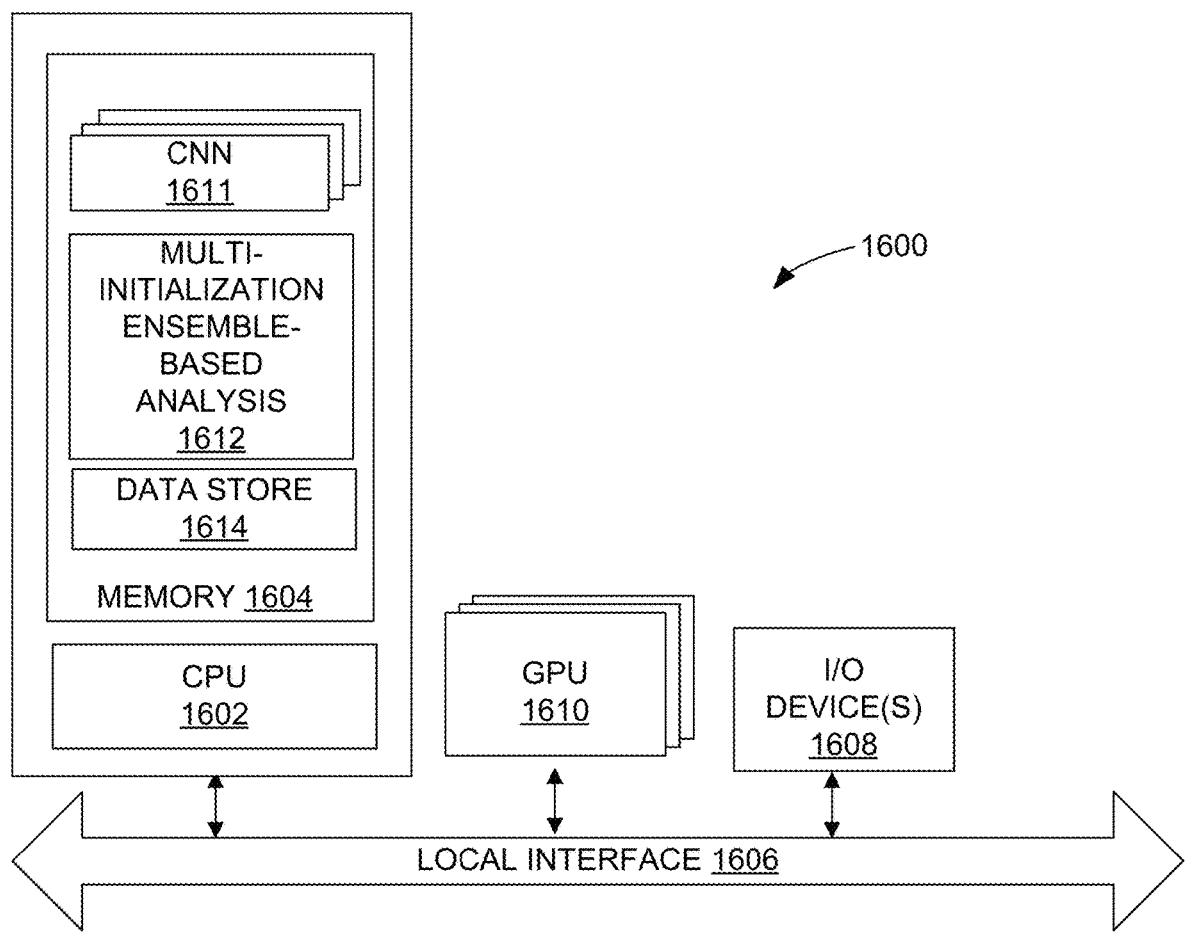
FIG. 16 shows a schematic block diagram of a computing device that can be used to implement various embodiments of the present disclosure

FIG. 16 depicts a schematic block diagram of a computing device 1600 that can be used to implement various embodiments of the present disclosure. An exemplary computing device 1600 includes at least one processor circuit, for example, having a processor 1602 and a memory 1604, both of which are coupled to a local interface 1606, and one or more input and output (I/O) devices 1608. The local interface 1606 may comprise, for example, a data bus with an accompanying address/control bus or other bus structure as can be appreciated. The computing device 1600 further includes Graphical Processing Unit(s) (GPU) 1610 that are coupled to the local interface 1606 and may utilize memory 1604 and/or may have its own dedicated memory. The CPU and/or GPU(s) can perform various operations such as image enhancement, graphics rendering, image/video processing, recognition (e.g., text recognition, object recognition, feature recognition, etc.), image stabilization, machine learning, filtering, image classification, and any of the various operations described herein.

Stored in the memory 1604 are both data and several components that are executable by the processor 1602. In particular, stored in the memory 1604 and executable by the processor 1602 are code for implementing different convolutional neural network (CNN) models 1611 and a multi-initialization ensemble-based analysis logic/instructions 1612. Also stored in the memory 1604 may be a data store 1614 and other data. The data store 1614 can include an image database for original images and adversarial images, and potentially other data. In addition, an operating system may be stored in the memory 1604 and executable by the processor 1602. The I/O devices 1608 may include input devices, for example but not limited to, a keyboard, mouse, etc. Furthermore, the I/O devices 1608 may also include output devices, for example but not limited to, a printer, display, etc.

Certain embodiments of the present disclosure can be implemented in hardware, software, firmware, or a combination thereof. If implemented in software, the multi-initialization ensemble-based analysis logic or functionality are implemented in software or firmware that is stored in a memory and that is executed by a suitable instruction execution system. If implemented in hardware, the multi-initialization ensemble-based analysis logic or functionality can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

Therefore, at least the following is claimed:

1. A method comprising: training a plurality of convolutional neural networks multiple times with different seed point initializations with a training set of images, wherein the images include original images and images modified by an adversarial attack; after training of the plurality of convolutional neural networks, providing an input image to the plurality of convolutional neural networks, wherein the input image has been modified by an adversarial attack; receiving a probability output for the input image from each of the plurality of convolutional neural networks, wherein the probability output comprises a probability that the image belongs to one or more categories; producing an ensemble probability output for the input image by combining the probability outputs from each of the plurality of convolutional neural networks; and labeling the input image as belonging to one of the one or more categories based on the ensemble probability output.

2. The method of claim 1, wherein the plurality of convolutional neural networks include convolutional neural networks of different convolutional neural network architectures.

3. The method of claim 2, wherein the plurality of convolutional neural networks further include a convolutional neural network at different seed point initializations.

4. The method of claim 1, wherein the plurality of convolutional neural networks further include a convolutional neural network at different seed point initializations.

5. The method of claim 1, wherein the ensemble probability output image is combined by averaging the probability outputs from each of the plurality of convolutional neural networks.

6. The method of claim 1, wherein the input image and the training set of images comprise a computed tomography scan.

7. The method of claim 6, wherein the one or more categories involve a cancer diagnosis for a subject of the computed tomography scan.

8. The method of claim 1, wherein the input image and the training set of images comprise 2D images.

9. The method of claim 1, wherein the input image and the training set of images comprises 3D images.

10. The method of claim 1, wherein the adversarial attack is a Fast Gradient Signed Method (FGSM) adversarial attack.

11. The method of claim 1, wherein the adversarial attack is a one pixel adversarial attack.

12. The method of claim 1, wherein the images modified by an adversarial attack comprise average ensemble attack images.

13. The method of claim 1, wherein the images modified by an adversarial attack comprise maximum value ensemble attack images.

14. A system comprising:
a processor:
a tangible, non-transitory memory configured to communicate with the processor, the tangible, non-transitory memory having instructions stored thereon that, in response to execution by the processor, cause the processor perform operations comprising:
training each of a plurality of convolutional neural networks multiple times with different seed point initializations with a training set of images, wherein the images include original images and images modified by an adversarial attack;
after training of the plurality of convolutional neural networks, providing an input image to the plurality of convolutional neural networks, wherein the input image has been modified by an adversarial attack;
receiving a probability output for the input image from each of the plurality of convolutional neural networks, wherein the probability output comprises a probability that the image belongs to one or more categories;
producing an ensemble probability output for the input image by combining the probability outputs from each of the plurality of convolutional neural networks; and
labeling the input image as belonging to one of the one or more categories based on the ensemble probability output.

15. The system of claim 14, wherein the plurality of convolutional neural networks include convolutional neural networks of different convolutional neural network architectures.

16. The system of claim 15, wherein the plurality of convolutional neural networks further include a convolutional neural network at the different seed point initializations.

17. The system of claim 14, wherein the ensemble probability output image is combined by averaging the probability outputs from each of the plurality of convolutional neural networks.

18. The system of claim 14, wherein the input image and the training set of images comprise a computed tomography scan.

19. A non-transitory, tangible computer readable storage medium having instructions stored thereon that in response to execution by a computing device, cause the computing device to perform operations comprising:
training each of a plurality of convolutional neural networks multiple times with different seed point initializations with a training set of images, wherein the images include original images and images modified by an adversarial attack;
after training of the plurality of convolutional neural networks, providing an input image to the plurality of convolutional neural networks, wherein the input image has been modified by an adversarial attack;
receiving a probability output for the input image from each of the plurality of convolutional neural networks, wherein the probability output comprises a probability that the image belongs to one or more categories;
producing an ensemble probability output for the input image by combining the probability outputs from each of the plurality of convolutional neural networks; and
labeling the input image as belonging to one of the one or more categories based on the ensemble probability output.

20. The computer readable storage medium of claim 19, wherein the ensemble probability output image is combined by averaging the probability outputs from each of the plurality of convolutional neural networks.

* * * * *